(12) United States Patent
Sajja et al.

(10) Patent No.: US 7,772,398 B2
(45) Date of Patent: Aug. 10, 2010

(54) PROCESS FOR MAKING CRYSTALLINE FORM I OF CLOPIDOGREL HYDROGEN SULPHATE

(75) Inventors: Eswaraiah Sajja, Hyderabad (IN); Raghupathi Reddy Anumula, Hyderabad (IN); Bhaskara rao Venkata Uppala, Hyderabad (IN)

(73) Assignees: Dr. Reddy's Laboratories, Inc., Bridgewater, NJ (US); Dr. Reddy's Laboratories Limited, Hyderabad (IN)

( * ) Notice: Subject to any disclaimer, the term of this patent is extended or adjusted under 35 U.S.C. 154(b) by 929 days.

(21) Appl. No.: 11/079,881

(22) Filed: Mar. 11, 2005

(65) Prior Publication Data

US 2006/0205766 A1    Sep. 14, 2006

(51) Int. Cl.
*C07D 495/04* (2006.01)
(52) U.S. Cl. ................................ 546/114; 514/301
(58) Field of Classification Search ............. 546/114; 514/301
See application file for complete search history.

(56) References Cited

U.S. PATENT DOCUMENTS

| 4,847,265 A | 7/1989 | Badore et al. |
| 6,429,210 B1 | 8/2002 | Bousquet et al. |
| 6,767,913 B2 * | 7/2004 | Lifshitz et al. .............. 514/301 |
| 7,291,735 B2 * | 11/2007 | Mukarram et al. .......... 546/114 |
| 2006/0041136 A1 * | 2/2006 | Veverka et al. .............. 546/114 |

FOREIGN PATENT DOCUMENTS

| WO | WO 2004/020443 A1 | 3/2004 |
| WO | WO2004/020443 | * 11/2004 |
| WO | WO2005/100364 | * 10/2005 |

* cited by examiner

*Primary Examiner*—Celia Chang
(74) *Attorney, Agent, or Firm*—Robert A. Franks; Lee C. Banks; Anjum Swaroop

(57) ABSTRACT

A process for preparation of crystalline Form I of clopidogrel hydrogen sulphate, that include separating the crystalline Form I of clopidogrel hydrogen sulphate from a solution of clopidogrel freebase in a solvent, which is 2-propanol or 2-butanol is provided.

12 Claims, 3 Drawing Sheets

US 7,772,398 B2

PROCESS FOR MAKING CRYSTALLINE FORM I OF CLOPIDOGREL HYDROGEN SULPHATE

BACKGROUND OF THE INVENTION

Clopidogrel hydrogen sulphate is an anti-platelet drug. Both the racemic form of the drug and optical isomers are known in the art. See, e.g., U.S. Pat. Nos. 6,429,210 and 4,847,265. The '210 patent discloses that clopidogrel hydrogen sulphate can exist in two polymorphic forms (designated as Form I and Form II) and provides analytical characterization for the polymorphs.

SUMMARY OF THE INVENTION

The inventors of the present invention had discovered that the prior art processes present substantial difficulties in producing Form I of clopidogrel hydrogen sulphate in a consistent manner. The invention provides an improved process for making Form I of clopidogrel hydrogen sulphate. In accordance with one aspect, the invention provides a process for preparation of crystalline Form I of clopidogrel hydrogen sulphate, which process includes separating the crystalline Form I of clopidogrel hydrogen sulphate from a solution of clopidogrel freebase in a solvent, which is 2-propanol or 2-butanol.

DETAILED DESCRIPTION OF THE PREFERRED EMBODIMENTS

Figure 1:
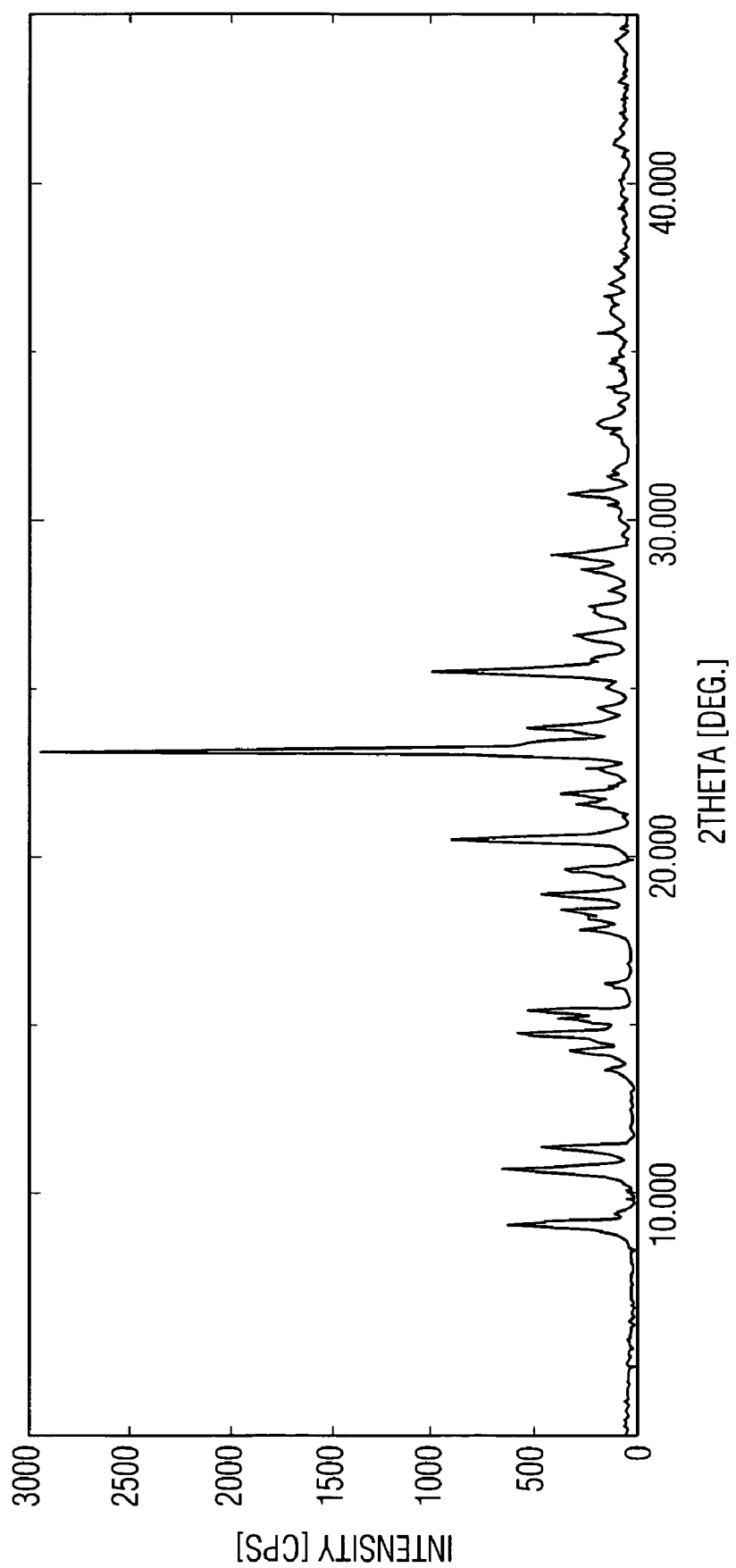
FIG. 1 shows an X-Ray Powder Diffractogram of an exemplary batch of Form I of clopidogrel hydrogen sulphate obtained in accordance with process of the invention.

Unless defined otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

The term "isolating" is used to indicate separation of the compound being isolated regardless of the purity of the isolated compound from any unwanted substance which presents with the compound as a mixture. Thus, degree of the purity of the isolated or separated compound does not affect the status of "isolating".

The term "separating from a solvent" with respect to the crystalline solids described herein means obtaining a solid of specified characteristics from a starting solution.

The term "treating" means adding the stated reagent or materials to the thing being treated.

The term "forming a solution" means obtaining a solution of a substance in a solvent in any manner.

The term "evaporation residue" means residual substance (solid or semi-solid) obtained by evaporating a solvent in which the substance was previously dissolved.

The term "inoculating" has the same meaning as the term "seeding," and means adding previously obtained solid to facilitate crystallization. Thus, the term "seeding crystals" with respect to claimed process means powder of previously obtained crystalline Form I of clopidogrel hydrogen sulphate.

The term "dichloromethane solvent" means a solvent containing dichloromethane. The term does not exclude solvents containing trace amounts of other solvents.

"Clopidogrel hydrogen sulphate" is a hydrogen sulphate salt of S enantiomer of (2-chlorophenyl) 6,7-dihydro-thieno[3,2-c]pyridine-5(4H)-acetic acid methyl ester. It has the structural formula:

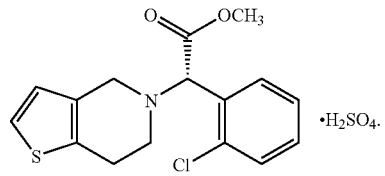

"Clopidogrel freebase" is a free species of S enantiomer of (2-chlorophenyl) 6,7-dihydro-thieno[3,2-c]pyridine-5(4H)-acetic acid methyl ester. It has the formula:

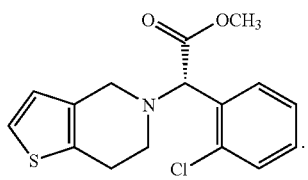

It should be understood that there exist equilibrium between a free species and an acid addition salt form of a compound capable of forming acid addition salts (e.g., by virtue of having a basic atom in the molecule). Thus, the presence of small amount of a salt form of clopidogrel in the starting solution described herein cannot be excluded.

"Camphor sulphonic salt of clopidogrel" is an acid addition salt of clopidogrel freebase and camphor sulphonic acid.

Polymorphic forms of clopidogrel hydrogen sulphate are known. See, e.g., European Patent No. 281459 (the "459 patent") and U.S. Pat. No. 6,429,210 (the '210 patent), both incorporated herein by reference in their entirety. The '210 patent discloses and defines two polymorphic forms of the drug: Form I and Form II. The solid that the '210 patent defines as Form I had been previously disclosed in the '459 patent. The solid that the '210 patent defines as Form II is disclosed and claimed in the '210 patent itself. For the purposes of this description and claims of the present invention, the term "crystalline Form I of clopidogrel hydrogen sulphate" is the polymorphic form denoted as Form I in the '210 patent. The '210 patent is herein also incorporated by reference specifically for the purposes of providing a) the reference analytical information (XRD, IR spectra, and melting point data) for Forms I and II, and b) a method of preparation of optically active clopidogrel camphor sulfonate. Portions of this specifically incorporated information are identified particularly further. Identification of solids obtained by the process of the invention can be made by comparing analytical data for the obtained solids with the reference analytical information provided in the '210 patent. Of course, it should be undestood that operator, instrument and other similar issues may result in some margin of error with respect analytical characterization of the solid.

The '459 patent describes isolation of crystalline Form I of clopidogrel by dissolution of clopidogrel freebase in acetone cooled on ice, followed by addition of concentrated sulphuric acid that leads to precipitation of the hydrogen sulphate salt. The '210 patent describes preparation of Form II, as well as Form I. The Form II of the '210 patent is also isolated from acetone. To obtain specifically Form II from the same solvent from which Form I is also precipitated, the '210 patent teaches maintaining certain process parameters. The inventors of the present invention had found that the use of acetone does not provide a reliable, consistent methodology to prepare Form I. The inventors had recognized that in using acetone small changes in manufacturing parameters might lead to contamination of the desired solid Form I with Form II impurities. The inventors had found that the use of 2-butanol (also known as secondary butyl alcohol) as a solvent permits reliable preparation of Form I of clopidogrel hydrogen sulphate. The invention also contemplates the use of 2-propanol (also known as isopropanol), although 2-butanol is preferred.

Thus, Form I of clopidogrel hydrogen sulphate may be separated as a solid from a solution of clopidogrel freebase in 2-butanol or 2-propanol. The solution of clopidogrel freebase may be prepared by mixing clopidogrel freebase and the solvent together and stirring for dissolution. The solution may then be filtered to remove particulate matter. Once the solution of the freebase is obtained, sulphuric acid is added to convert the freebase to the hydrogen sulphate salt. Optionally, either before or after sulphuric acid addition, the solution may be seeded with previously obtained crystals of the Form I. The mass is then stirred until crystallization of the solid is complete. The solid is filtered, washed, and dried. The process conditions are further illustrated in the Examples.

The starting clopidogrel freebase needed to form the solution from which Form I is separated may be obtained in any manner. Preferably, clopidogrel freebase is obtained from camphor sulfonic acid salt of clopidogrel, which itself may be prepared in any manner. For example, preparation of suitable camphor sulfonic acid salt of clopidogrel is described in the '210 patent, a portion of which (col. 9, lines 1-22) is incorporated for this purpose specifically.

In one variant of the process of the invention, a camphor sulphonic salt of clopidogrel is dissolved in an organic solvent, preferably dichloromethane-containing solvent, and treated with an aqueous solution of an inorganic base, preferably sodium carbonate, to convert the acid addition salt into clopidogrel freebase in solution. The reaction mass after treatment is a two-phose system containing an aqueous phase and an organic phase. The organic phase primarily includes dichloromethane and clopidogrel freebase. Then, organic phase is separated and the solvent is removed to provide an evaporation residue of clopidogrel freebase. 2-butanol or 2-propanol is then added to the evaporation residue to form a solution; to which concentrated sulphuric acid is added to convert the freebase to the hydrogen sulphate salt. The solution is stirred and maintained while Form I crystallizes out. The solid is filtered, washed and dried. The process conditions are further illustrated in the Examples.

Figure 2:
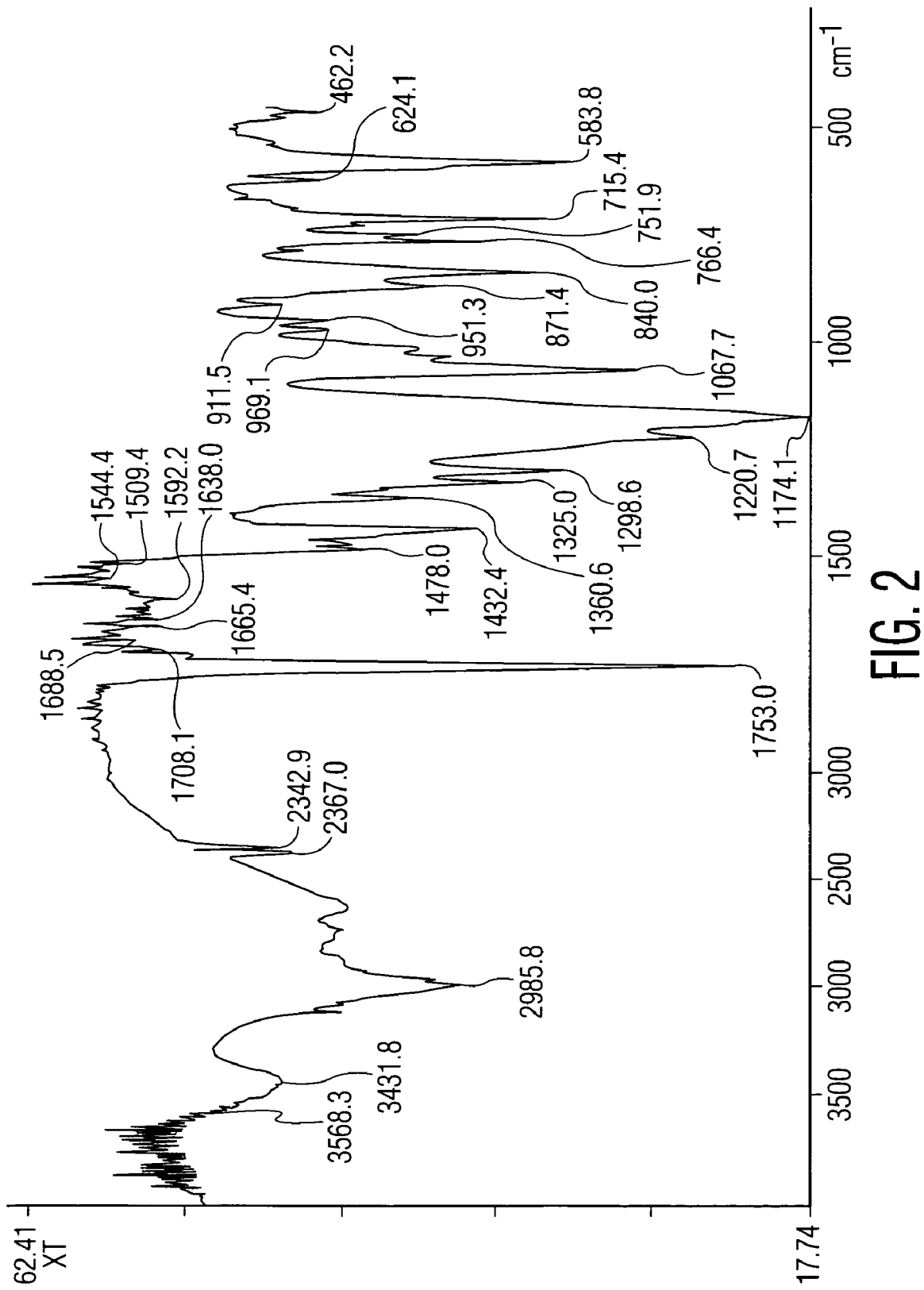
FIG. 2 shows an IR spectra of an exemplary batch of Form I of clopidogrel hydrogen sulphate obtained in accordance with process of the invention.

Analytical characterization of the solid(s) obtained in accordance with the process of the invention was carried out by using X-ray powder diffraction and/or infrared spectroscopy. Melting points of the solids were also obtained. The X-ray powder diffraction patterns were measured on a Bruker Axs, D8 advance Powder X-ray diffractometer with Cu K alpha-1 radiation source (voltage of 50 kV; current: 25 mA). The IR spectra were obtained on Perkin Elmer spectrometer (KBr tablets, 4 scans, resolution of 4 $cm^{-1}$). The analytical data obtained for the solids were compared with data provided in the '210 patent, which portions (especially, FIGS. 1 and 4 of the '210 patent, and portions of columns 4-5 that relate to Form I) are incorporated for this purpose specifically. FIGS. 1 and 2 provides characteristic XRD and IR spectra, respectively, of exemplary batches of crystalline Form I produced in the process of the invention.

The examples provided below are illustrative and are not intended to limit the scope of the claimed invention.

EXAMPLE 1

80 mls of isopropanol and 20 grams of clopidogrel freebase were stirred at 25-30° C. until clopidogrel freebase was dissolved. 3.4 mls of concentrated sulphuric acid were slowly added (15-20 minutes) while maintaining a temperature of 25-30° C. The mass was stirred at 25-30° C. and maintained at this temperature for about 3-4 hours. The precipitated solid was filtered. The filtrate was kept to obtain additional crops of the crystallizing solid. The first isolated crop was washed with 10 mls of isopropanol, and dried under vacuum at 25-30° C. to constant weight. 4.6 grams of solid crystalline Form I of clopidogrel hydrogen sulphate were obtained. Additional solid (Form II) was obtained from the set-aside mother liquors.

EXAMPLE 2

1600 mls of isopropanol and 200 grams of clopidogrel freebase were charged into a round-bottom flask and stirred at 25-30° C. until clopidogrel freebase was dissolved. The solution was filtered and cooled to about 25° C. 12 grams of crystalline Form I of clopidogrel hydrogen sulphate were added as a seeding material. 34 mls of concentrated sulphuric acid were slowly added while maintaining a temperature of 25-30° C. The mass was stirred at 25-30° C. and maintained at this temperature for approximately an hour. The formed precipitate was filtered. The mother liquor was put aside to obtain additional crops of precipitating solid. The first crop was dried to constant weight at 60-70° C., and provided 15.2 grams of crystalline Form I of clopidogrel hydrogen sulphate. Additional amounts of solid clopidogrel hydrogen sulphate (Form I and Form II) were isolated from the put-aside mother liquors.

EXAMPLE 3

1000 mls of 2-butanol and 50 grams of clopidogrel base were stirred at 25-30° C. until clopidogrel base was dissolved. The solution was filtered and cooled to about 10-15° C. 10 grams of crystalline Form I of clopidogrel hydrogen sulphate were added as a seeding material. 8.5 mls of concentrated sulphuric acid were slowly added while maintaining a temperature of 10-15° C. The mass was warmed to about 20° C. stirred and maintained at 25-30° C. until crystallization was complete. The precipitate was filtered. The solid was washed with 50 mls of 2-butanol and dried to constant weight at 60-70° C. 59.2 grams of crystalline Form I of clopidogrel hydrogen sulphate was isolated.

EXAMPLE 4

A mixture of Methyl(S)-α-(2-Chlorophenyl)-6,7-dihydrothieno[3,2-c]pyridine-5-(4H)-acetate camphorsulfonic acid (70.0 grams) and dichloromethane (300.0 ml) was cooled to 0-5° C. A 4.4% aqueous solution of sodium carbonate was slowly added until the pH of the reaction mixture is from 7.5 to 8.0 (about 7.0 grams of sodium carbonate in deionized water). The reaction mass was stirred for 20-30 minutes and the mass was allowed to settle. The organic (bottom) layer was separated. The aqueous layer was extracted twice with dichloromethane (2×100.0 ml). The organic layers were combined and twice washed with water (2×100.0 ml) and the aqueous layer was removed. The mass was heated to remove dichloromethane at a temperature of the mass below 50° C., the mass was cooled to 40-45° C., and the solvent was distilled off under reduced pressure. About 80 mls of fresh 2-butanol was added to the residue. The traces of dichloromethane were removed by co-distillation with 2-butanol under reduced pressure (about 5 mm/Hg) at a temperature below 55° C. until a residue of clopidogrel base was obtained.

1200 mls of 2-butanol were added to the residue of clopidogrel base and stirred for dissolution. The resulting solution was treated with activated carbon, stirred for 5-10 minutes, and filtered. The resulting clear solution was cooled to 25-27° C. 6.38 mls of concentrated sulphuric acid were slowly (15-20 minutes) added. The solution was seeded with about 0.4 gram of Form I of clopidogrel hydrogen sulphate. The mass was cooled to 24-26° C. and maintained at this temperature for about 2-3 hours. The mass was further maintained at this temperature, with stirring, for additional about 4-6 hours until onset of crystallization. The mass further cooled to 22-24° C. and held until the crystallization was complete. The precipitated crystalline Form I of clopidogrel hydrogen sulphate was filtered, washed with 2-butanol (about 60 mls) and dried under vacuum. The solid was further washed with cyclohexane (about 60 mls). The wet material was dried at 70-80° C. for 3-4 hours and further dried at 95-100° C. under vacuum for about 7-8 hours. The temperature of the drier was cooled to 25-30° C. and crystalline Form-I of clopidogrel hydrogen sulphate was isolated.

EXAMPLE 5

625 mls of dichloromethane were charged into a round-bottom flask. 100 grams of Methyl(S)-α-(2-Chlorophenyl)-6,7-dihydrothieno[3,2-c]pyridine-5-(4H)-acetate camphorsulfonic acid were added and the mass was cooled to 0-5° C. with stirring. A 10% aqueous solution of sodium carbonate (10 grams in 100 mls of deionized water) was slowly added until the pH of the reaction mixture is from 7.5 to 8.0. The reaction mass was stirred for 20-30 minutes and the mass was allowed to settle. The organic layer was separated. The aqueous layer was extracted twice with dichloromethane (2×150.0 ml). The organic layers were combined and twice washed with water (2×150.0 ml) and the aqueous layer was removed. The mass was heated to remove dichloromethane at a temperature of the mass below 55° C., the mass was cooled to 30-35° C., vacuum was applied, and the solvent was distilled off under reduced pressure at a temperature of the mass below 55° C. About 425 mls of fresh 2-butanol was added to the residue. The traces of dichloromethane were removed by co-distillation with 2-butanol under reduced pressure at a 30-35° C. until a residue of clopidogrel base was obtained.

Figure 3:
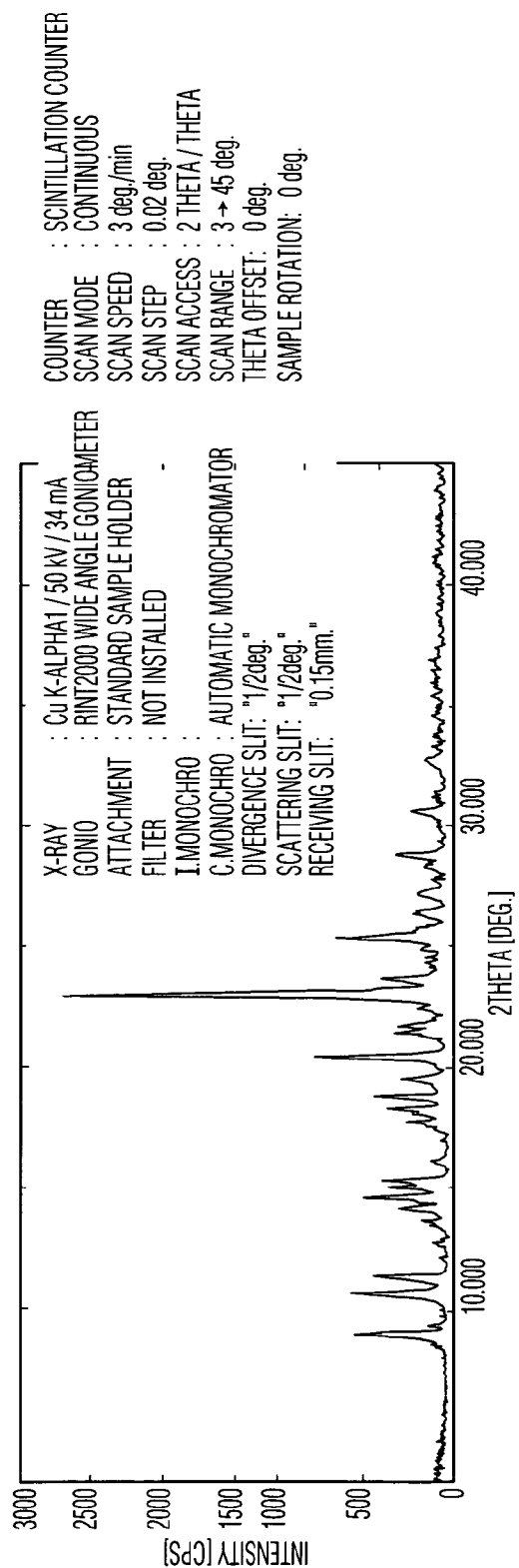
FIG. 3 shows an X-Ray Powder Diffractogram of the solid (Form I of clopidogrel hydrogen sulphate) obtained in accordance with Example 5.

875 mls of 2-butanol were added to the residue of clopidogrel base and stirred for dissolution. The resulting solution was treated with 5 grams of activated carbon, stirred for 30-45 minutes, and filtered. The carbon bed was washed with 250 mls of 2-butanol. The clear solution was cooled to 10-15° C. 8.68 mls of concentrated sulphuric acid were slowly added with temperature maintained at 10-15° C. The mass was warmed to 20-30° C. and maintained at this temperature for about 15-18 hours until the crystallization was complete. The precipitated crystalline Form I of clopidogrel hydrogen sulphate was filtered, washed with 100 mls of 2-butanol, and suck-dried under vacuum. The mother liquor was put aside. The solid was further washed with 100 mls of cyclohexane. The wet material was dried at 70-80° C. to constant weight. The temperature of the drier was cooled to 25-30° C. and solid crystalline Form I of clopidogrel hydrogen sulphate was isolated (26.6 grams). XRD of the solid is provided in FIG. 3. 33.4 grams of crystalline Form II of clopidogrel hydrogen sulphate were isolated from the mother liquor.

EXAMPLE 6

1000 mls of 2-butanol and 50 grams of clopidogrel base were stirred at 25-30° C. until clopidogrel base was dissolved. The solution was filtered and cooled to about 10-15° C. 8.5 mls of concentrated sulphuric acid were slowly added while maintaining a temperature of 10-15° C. The mass was warmed to about 20° C. stirred and maintained at 25-30° C. for about 13-15 hours. If no crystallization was observed, a small amount of seeding crystals of clopidogrel hydrogen sulphate were added. The mass was maintained until crystallization was complete. The precipitate was filtered. The solid was washed with 50 mls of 2-butanol and dried to constant weight at 60-70° C. 59.6 grams of crystalline Form I of clopidogrel hydrogen sulphate was isolated.

Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A process for preparation of crystalline Form I of clopidogrel hydrogen sulphate, said process comprising treating a solution of clopidogrel freebase in a solvent, said solvent being 2-propanol, with sulphuric acid at a temperature of from 25-30° C. for a time sufficient to obtain crystalline Form I of clopidogrel hydrogen sulphate.

2. The process of claim 1, wherein said process further includes inoculating said solution with seeding crystals of Form I of clopidogrel hydrogen sulphate.

3. The process of claim 2, wherein the seeding crystals are added before addition of sulphuric acid.

4. The process of claim 2, wherein the seeding crystals are added after addition of sulphuric acid.

5. The process of claim 1, further comprising forming said solution of clopidogrel freebase by adding said solvent to an evaporation residue of clopidogrel freebase.

6. The process of claim 5, further comprising providing a solution of a camphor sulphonic salt of clopidogrel in a dichloromethane solvent, treating said dichloromethane solution with an aqueous inorganic base thereby obtaining an aqueous phase and an organic phase, separating said organic phase from said aqueous phase, and distilling off the solvent, thereby obtaining said evaporation residue of clopidogrel freebase.

7. A process for preparation of crystalline Form I of clopidogrel hydrogen sulphate, said process comprising treating a solution of clopidogrel freebase in a solvent, said solvent being 2-butanol, with sulphuric acid at a temperature of from 10-30° C. for a time sufficient to obtain crystalline Form I of clopidogrel hydrogen sulphate.

8. The process of claim 7, wherein said process further includes inoculating said solution with seeding crystals of Form I of clopidogrel hydrogen sulphate.

9. The process of claim 8, wherein the seeding crystals are added before addition of sulphuric acid.

10. The process of claim 8, wherein the seeding crystals are added after addition of sulphuric acid.

11. The process of claim 7, further comprising forming said solution of clopidogrel freebase by adding said solvent to an evaporation residue of clopidogrel freebase.

12. The process of claim 11, further comprising providing a solution of a camphor sulphonic salt of clopidogrel in a dichloromethane solvent, treating said dichloromethane solution with an aqueous inorganic base thereby obtaining an aqueous phase and an organic phase, separating said organic phase from said aqueous phase, and distilling off the solvent, thereby obtaining said evaporation residue of clopidogrel freebase.

* * * * *